US00PP23966P2

(12) United States Plant Patent
Ault et al.

(10) Patent No.: US PP23,966 P2
(45) Date of Patent: Oct. 8, 2013

(54) ***ASTER PLANT* NAMED 'BRIDAL VEIL'**

(50) Latin Name: ***Symphyotrichum* hybrid**
Varietal Denomination: Bridal Veil

(75) Inventors: James Robert Ault, Libertyville, IL (US); Catherine S. Thomas, Northfield, IL (US)

(73) Assignee: Chicagoland Grows, Inc., Glencoe, IL (US)

( * ) Notice: Subject to any disclaimer, the term of this patent is extended or adjusted under 35 U.S.C. 154(b) by 87 days.

(21) Appl. No.: 13/385,516

(22) Filed: Feb. 23, 2012

(51) Int. Cl.
*A01H 5/00* (2006.01)

(52) U.S. Cl.
USPC ..... Plt./355

(58) Field of Classification Search
USPC ..... Plt./355
See application file for complete search history.

*Primary Examiner* — Annette Para
(74) *Attorney, Agent, or Firm* — Penny J. Aguirre

(57) ABSTRACT

A new cultivar of *Aster*, 'Bridal Veil', characterized by its spreading and weeping plant habit, its numerous large white capitula, its mature height of about 60 cm (24 inches) and spread of about 1.4 m (54 inches), its good resistance to rust and powdery mildew, and its hardiness in at least U.S.D.A. Zones 5 to 7.

2 Drawing Sheets

Botanical classification: *Symphyotrichum* hybrid.
Variety denomination: 'Bridal Veil'.

BACKGROUND OF THE INVENTION

The present invention relates to a new and distinct cultivar of *Symphyotrichum* hybrid (previously *Aster* hybrid), botanically known as *Symphyotrichum* 'Bridal Veil', and will be referred to hereafter by its cultivar name, 'Bridal Veil'. 'Bridal Veil' is a new herbaceous perennial suitable for landscape plantings.

The new cultivar is the result of a controlled breeding program conducted by the Inventors in Glencoe, Ill. The intent of the program is to develop new cultivars of *Aster* that are hardy in U.S.D.A. Zone 5, disease resistant, and adaptable to typical landscape growing conditions. The new cultivar arose from a self-pollination of 'Snow Flurry' (not patented) in October of 2002. 'Bridal Veil' was selected as a single unique plant from the resulting seedlings of the cross in October of 2007.

The new cultivar was first asexually propagated by shoot tip cuttings by one of the Inventors in Glencoe, Ill. in June of 2008. Asexual propagation has determined that the characteristics of this cultivar are stable and are reproduced true to type in successive generations.

SUMMARY OF THE INVENTION

The following traits have been repeatedly observed and represent the characteristics of the new *Aster*. These attributes in combination distinguish 'Bridal Veil' as a unique cultivar of *Aster*.

1. 'Bridal Veil' exhibits a spreading and weeping plant habit.
2. 'Bridal Veil' exhibits numerous large white capitula.
3. 'Bridal Veil' reaches a mature height of about 60 cm (24 inches) and a spread of about 1.4 m (54 inches).

4. 'Bridal Veil' has shown good resistance to rust and powdery mildew when grown in comparison trials with other cultivars of *Aster*.
5. 'Bridal Veil' is hardy in at least U.S.D.A. Zones 5 to 7.

The new cultivar of *Aster* can be readily distinguished from other cultivars of *Aster* known to the Inventors. The seed parent of 'Bridal Veil', 'Snow Flurry', differs from 'Bridal Veil' in being shorter in height, in having a prostrate plant habit, and in having smaller capitula. 'Bridal Veil' can be most closely compared to *Symphyotrichum ericoides* 'First Snow' (not patented) and *Symphyotrichum pilosum* var. *pringlei* 'Monte Cassino' (not patented). Both cultivars are similar to 'Bridal Veil' in having a profusion of white capitula in September and October in northern Illinois (U.S.D.A. zone 5a). 'First Snow' differs from 'Bridal Veil' in having upright stems that form an irregular mounded plant habit that is less spreading. 'Monte Cassino' differs from 'Bridal Veil' in having upright stems with an upright and mounded plant habit, in being taller in height and less spreading, and in having smaller capitula.

BRIEF DESCRIPTION OF THE DRAWING

The accompanying colored photographs illustrate the overall appearance and distinct characteristics of a five year-old plant of the new *Aster* as grown outdoors in a trial plot in Glencoe, Ill.

DETAILED BOTANICAL DESCRIPTION

Figure 1:
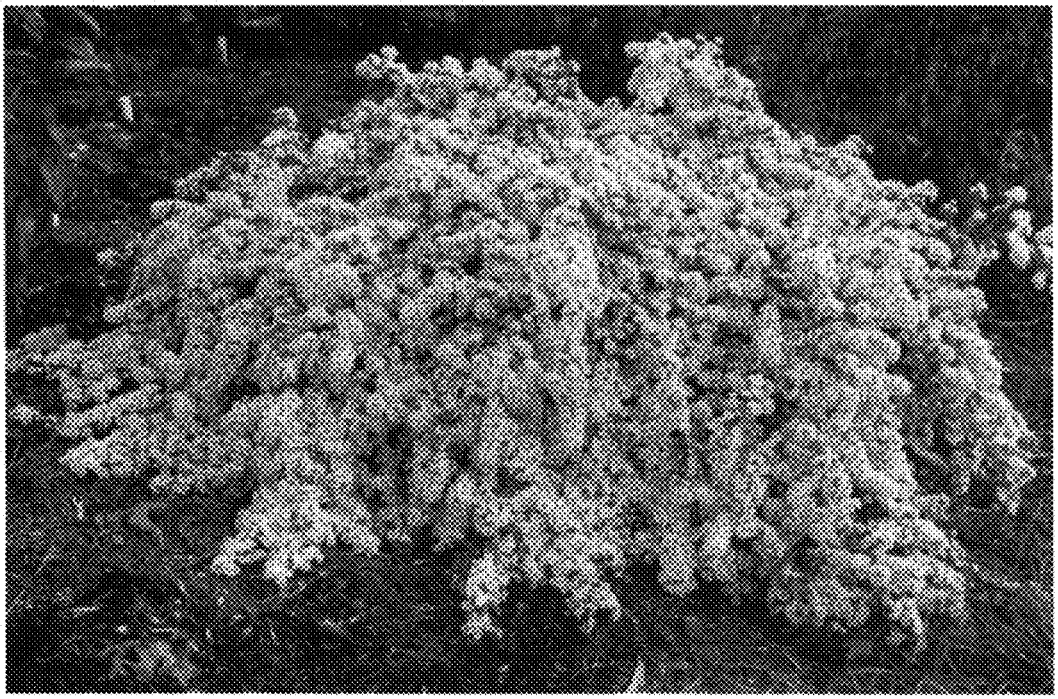
FIG. 1 was taken in October and provides a view of the plant habit of 'Bridal Veil' in bloom.
Figure 2:
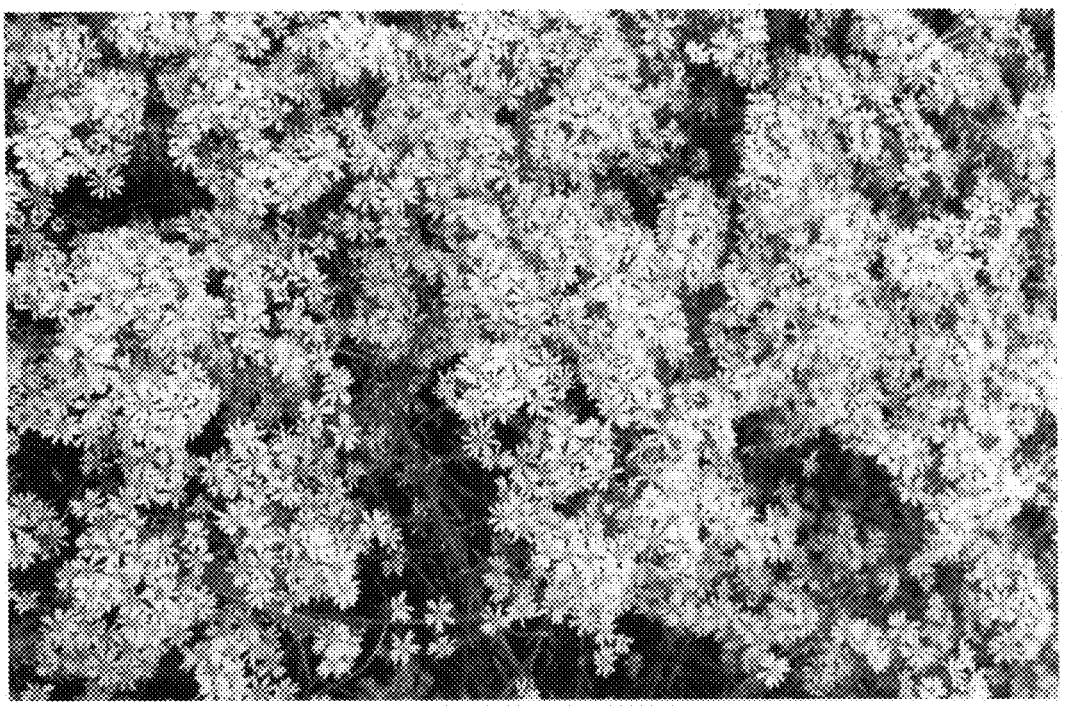
FIG. 2 was taken in October and provides a view of the inflorescences of 'Bridal Veil'.
Figure 3:
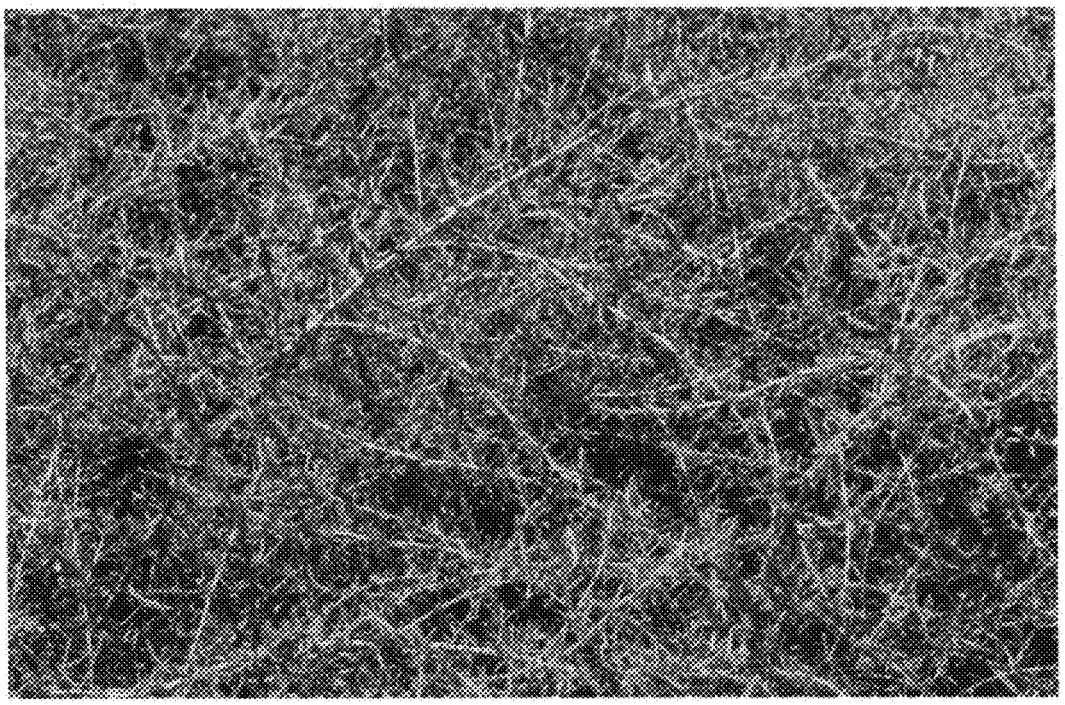
FIG. 3 was taken in July and provides a view of the branches of 'Bridal Veil'. The colors in the photographs are as close as possible with digital photography techniques available, the color values cited in the detailed botanical description accurately describe the colors of the new *Aster*.

The following is a description of one year old plants of the new cultivar as grown outdoors in 2-quart containers. The description of the plant habit and mature height and spread were observed on 5 year-old plants of the new cultivar as grown in a trial bed in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming season*.—Third week of September until the end of October with two weeks of peak bloom (almost 100% inflorescence coverage) in early October in northern Illinois.

*Plant habit*.—Herbaceous perennial, initially upright early in the season and becoming lateral then pendulous (weeping) and spreading.

*Height and spread*.—Reaches a height of about 60 cm (24 inches) and a spread of about 1.4 m (54 inches) in five years of growth.

*Hardiness*.—At least in U.S.D.A. Zones 5 to 7.

*Diseases resistance*.—Has shown good resistance to rust and powdery mildew when grown in comparison trials with other cultivars of *Aster*.

*Root description*.—Fibrous.

*Propagation*.—Shoot tip cuttings, very high rooting rate.

*Growth rate*.—Vigorous in comparison to its seed parent.

Stem description:

*Stem color*.—New growth 144A, mature growth 165A.

*Stem surface*.—Pubescent.

*Stem size*.—Main stem; about 30 cm in length and 2.5 mm in width, lateral branches; variable with an average of 15 cm in length and 1 mm in width, flowering branchlets; an average of 1.7 cm in length and 0.8 mm in width.

*Branching habit*.—Main stem with an average of 15 horizontal lateral branches merging from main stem with an average of 12 branchlets per stem 9 cm in length.

*Branch internode length*.—Average of 5 mm between lateral branches and branchlets.

Foliage description:

*Leaf division*.—Simple.

*Leaf shape*.—Linear.

*Leaf base*.—Truncate.

*Leaf apex*.—Acute.

*Leaf margin*.—Entire.

*Internode length*.—Average of 3 mm.

*Leaf venation*.—Linear, not conspicuous, midrib recessed on upper surface, color same as leaf.

*Leaf attachment*.—Sessile.

*Leaf arrangement*.—Alternate.

*Leaf number*.—Average of 6 per 2 cm in stem length.

*Leaf surface*.—Glabrous and satiny on upper and lower surface.

*Leaf color*.—Young and mature, upper and lower surface; 138A.

*Leaf size* (*fully expanded*).—Average of 9 mm in length and 1.5 cm in width.

*Leaf fragrance*.—None.

Flower description:

*Inflorescence type*.—Composite, 1 to 3 capitula per flowering branchlet.

*Lastingness of individual capitula*.—Temperature dependent, under normal field conditions during the fall, typically last about 2 weeks.

*Fragrance*.—None.

*Quantity of capitula*.—About 600 per plant in a 2-quart container.

*Capitula buds*.—About 6 mm in depth and 3.5 mm in diameter, oblong in shape, 144A in color with apex NN155B.

*Capitula size*.—About 1.8 cm in diameter and 7 mm in depth, diameter of disk about 5 mm.

*Peduncle*.—Held at about a 45° angle to flowering branchlet, texture is pubescent, an average of 5 mm in length and 0.8 mm in width, color is 144A and slightly suffused with 165A, an average of 4 leaves, similar in characteristics to branchlet leaves.

*Involucral bracts* (*phyllaries*).—About 14, 138A in color, spatulate in shape, about 3 mm in length and 1 mm in width, puberulent surface.

Ray florets (pistillate):

*Number*.—Average of 14.

*Shape*.—Oblanceolate.

*Aspect*.—Primarily horizontal.

*Size*.—Average of 7 mm in length and 2 mm in width.

*Petal apex*.—Rounded.

*Petal base*.—Attenuate.

*Petal margins*.—Entire.

*Petal texture*.—Smooth, glabrous on upper and lower surface.

*Petal color*.—Opening and mature; upper and lower surface: NN155B.

Disk florets (perfect):

*Quantity*.—Average of 60.

*Shape*.—Tubular.

*Size*.—About 6 mm in length and 1 mm in width.

*Color*.—145D.

Reproductive organs:

*Presence*.—Disk flowers are perfect, ray flowers are carpellate.

*Gynoecium*.—1 Pistil per disk and ray floret, style is 6 mm in length and 145D in color.

*Androecium*.—5 stamens per disk floret, fused into tube, anther is 165C in color with filament 145D in color, pollen was not observed.

*Fruit and seed*.—None observed.

It is claimed:

1. A new and distinct cultivar of *Aster* plant named 'Bridal Veil' as described and illustrated herein.

* * * * *